US011964127B2

(12) United States Patent
Arthur, III et al.

(10) Patent No.: US 11,964,127 B2
(45) Date of Patent: Apr. 23, 2024

(54) EXTERNAL DRIVING MECHANISM

(71) Applicant: Atlanta Biomedical Corporation, Suwanee, GA (US)

(72) Inventors: William D. Arthur, III, Santa Rose Beach, FL (US); Julius Stempfle, Suwanee, GA (US); Chang-Jung Lee, Milton, GA (US)

(73) Assignee: Atlanta Biomedical Corporation, Suwanee, GA (US)

( * ) Notice: Subject to any disclaimer, the term of this patent is extended or adjusted under 35 U.S.C. 154(b) by 267 days.

(21) Appl. No.: 17/450,754

(22) Filed: Oct. 13, 2021

(65) Prior Publication Data
US 2023/0112837 A1  Apr. 13, 2023

(51) Int. Cl.
*A61M 5/142* (2006.01)
*A61M 5/145* (2006.01)

(52) U.S. Cl.
CPC .... *A61M 5/14236* (2013.01); *A61M 5/14546* (2013.01); *A61M 2005/14208* (2013.01); *A61M 5/1424* (2013.01); *A61M 2005/14506* (2013.01); *A61M 2205/3306* (2013.01); *A61M 2205/332* (2013.01)

(58) Field of Classification Search
CPC .......... A61M 5/14236; A61M 5/14546; A61M 5/1424; A61M 2005/14208; A61M 2005/14506; A61M 2205/3306; A61M 2205/332; A61M 5/1456
See application file for complete search history.

(56) References Cited

U.S. PATENT DOCUMENTS

| | | | | |
|---|---|---|---|---|
| 2004/0133166 A1* | 7/2004 | Moberg | ............. | A61M 5/1456 604/151 |
| 2007/0121230 A1* | 5/2007 | Klein | ...................... | A61M 5/31 359/886 |
| 2008/0319394 A1* | 12/2008 | Yodfat | ................ | F04B 43/1253 604/154 |
| 2010/0063447 A1* | 3/2010 | Stempfle | ............. | A61M 5/1456 604/151 |
| 2014/0188076 A1* | 7/2014 | Kamen | ..................... | F04B 1/26 604/154 |
| 2019/0351132 A1* | 11/2019 | Pippin | ............... | A61M 5/14566 |
| 2020/0316291 A1* | 10/2020 | Gibson | .................. | A61M 5/158 |
| 2022/0241496 A1* | 8/2022 | Katsunuma | ............ | G16H 20/17 |
| 2023/0079117 A1* | 3/2023 | Beeby | ............... | A61M 5/31501 606/194 |

* cited by examiner

*Primary Examiner* — Nathan R Price
*Assistant Examiner* — Haden Matthew Ritchie
(74) *Attorney, Agent, or Firm* — Wang Law Firm, Inc.

(57) ABSTRACT

A system comprises a syringe pump and a special designed syringe. The syringe pump includes a housing with a flange holder for receiving a flange of the syringe barrel, an electrical motor disposed inside the housing, a plurality of gears driven by the electrical motor, a leadscrew connected to the plurality of gears, and a cage housing for housing the leadscrew and for holding at least partially the plunger. The flange of the plunger inserts into the flange holder, the leadscrew engages the plunger and moves the plunger in and out of the syringe.

15 Claims, 6 Drawing Sheets

EXTERNAL DRIVING MECHANISM

FIELD OF THE INVENTION

The invention relates to pharmaceutical drug delivery, and more particularly, to a drug delivery system with a compact driving mechanism.

BACKGROUND OF THE INVENTION

The real estate in a patient room is valuable. Often there are many equipment in the patient room, including monitoring devices, breathing equipment, and drug delivery machines. Usually the drug is delivered through syringes mounted on automatic pumps that deliver the drug in the syringes. The size of the pumps is dictated by the size of the syringes; for large syringes, large pumps must be used.

Therefore, there is a need for a system that enables smaller pumps to be used for drug delivery, and it is to this apparatus the present invention is primarily directed.

SUMMARY OF THE INVENTION

The present invention provides a compact system for delivering medication to patients. The system comprises a syringe pump and a special designed syringe. The syringe pump delivers medication through a syringe with a plunger to a patient. The system comprises a housing with a flange holder for receiving the flange of the syringe barrel, an electrical motor disposed inside the housing, a plurality of gears driven by the electrical motor, a leadscrew with a leadscrew shaft connected to the plurality of gears, a cage housing for housing the leadscrew and for holding at least partially the plunger, and a force sensing plate mounted on a mounting support inside the housing.

In another embodiment, the invention is a syringe for delivering medication. The syringe comprises a barrel and a plunger, and the plunger further comprises a plurality of plunger supports, at least one of the plurality of supports has a plurality of tracks on a first side and a plurality of markings on a second side.

In yet another embodiment, the invention is a system for delivering medication. The system comprises a pump and a syringe. The syringe further comprises a barrel with a flange, and a plunger with a plurality of plunger supports and a semi-circular push-end. The pump further comprises a housing with a flange holder for receiving the flange and a plunger slot for receiving one of the plunger supports, and a leadscrew for engaging one of the plunger supports.

BRIEF DESCRIPTION OF THE DRAWINGS

Features and advantages of embodiments of the invention will become apparent as the following Detailed Description proceeds, and upon reference to the Drawings, where like numerals depict like elements, and in which.

DETAILED DESCRIPTION OF THE INVENTION

Syringe infusion pump plays a critical role in a hospital system by automatically delivering drugs at a prescribed rate. A syringe infusion pump allows different sizes of syringes to be loaded and the syringe infusion pump can sense the syringe size, apply a proper force to push the plunger, and deliver drug at a prescribed rate. The syringe infusion pump is able to sense the position of the plunger and also provide the proper force to push the plunger, sensing the pushing force on the plunger, and deliver the drug at an accurate rate.

Generally, the syringe infusion pump is designed with following components:
(a) Syringe Barrel Holder: to securely hold down the syringe barrel;
(b) Size Sensor: to sense the size of loaded syringe by the barrel holder;
(c) Plunger Driver with Force Sensor: to push the syringe plunger to deliver fluid and sense the pushing force;
(d) Plunger Holder: to prevent free flow (or siphoning) from an unrestrained syringe plunger;
(e) Mechanical Power Driving System (Motor/Leadscrew/Clutch/Track): to move the Plunger Driver;
(f) Position Sensor: to monitor the movement of the Track and hence the plunger position.

When the syringe infusion pump is used, a syringe is loaded on the syringe infusion pump and secured. The syringe infusion pump will automatically detect the size of the syringe. The syringe infusion pump generally can be programmed to deliver drug at a predefined rate. After the syringe is placed on the infusion pump, the plunger engages an external pushing mechanism that pushes the plunger causing the drug in the syringe to be delivered.

Figure 1:
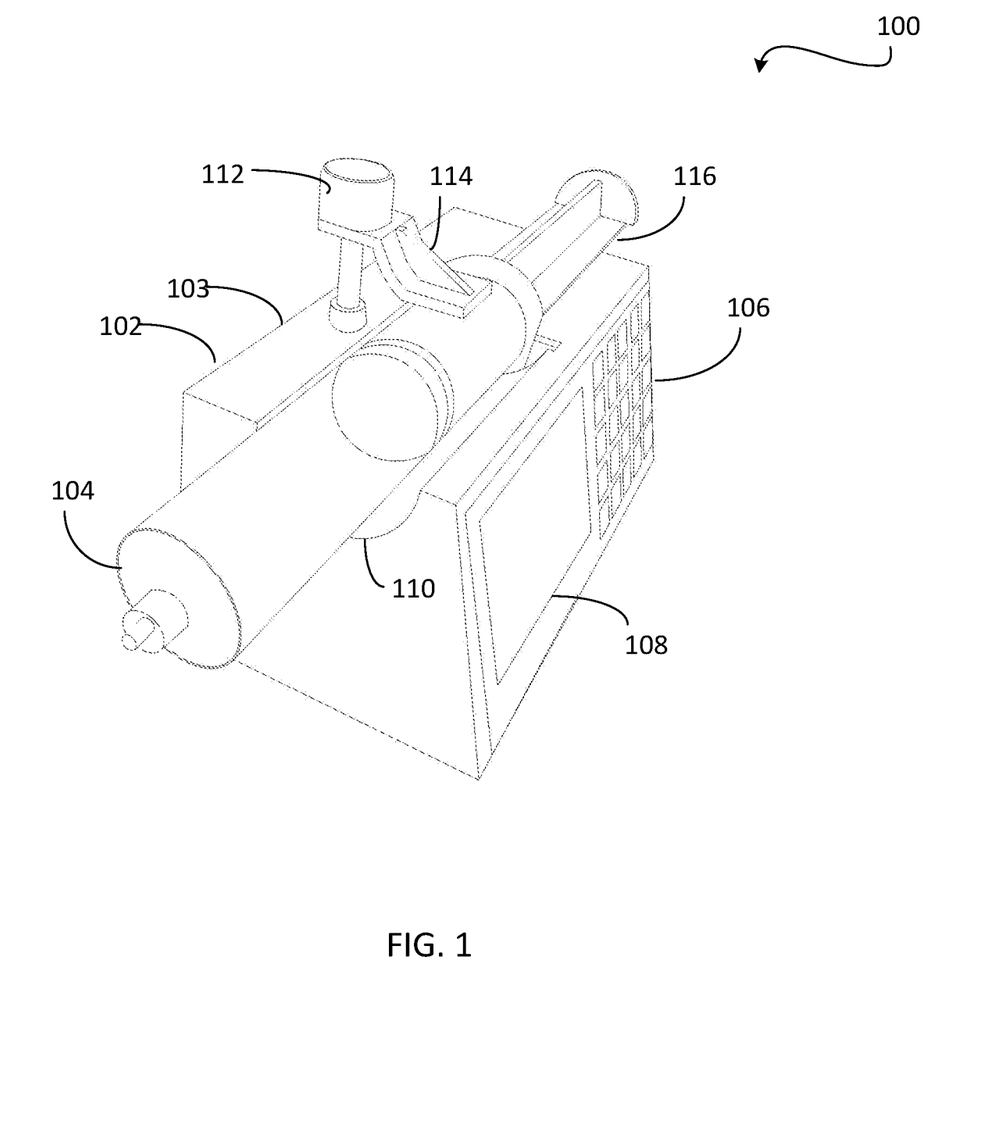
FIG. 1 is an illustration 100 of a new syringe infusion pump.

The present invention provides a system with a reduced foot print for delivery drug. The invention consists of a syringe infusion pump of reduced size and a new syringe with a new plunger. The pushing mechanism for the new plunger is internal to the syringe infusion pump. FIG. 1 is an illustration 100 of a new syringe infusion pump according to the present invention. The pump 102 has a housing 103 and a syringe 104 is placed on top of the housing 103 and secured by a syringe holder 112. The holder 112 has a spring (not shown) inside the housing 103 that enables a holding arm 114 attached to the syringe holder 112 to secure the syringe 104 against a semi-circular seat 110, so that the syringe 104 is secured in a fixed position. The syringe 104 has a plunger 116 that is partially inserted into the pump 102. The pump 102 has a display screen 108 and an input panel 106. The display screen 108 may be a touch screen that allows a user to input drug delivering commands and drug delivery parameters. The input panel 106 allows the user to input data and commands. The pump 102 has the necessary hardware, including an electrical circuit and a memory, to interface with the input panel 106, the display screen 108, and the driving mechanism (described later in FIG. 4).

Figure 2:
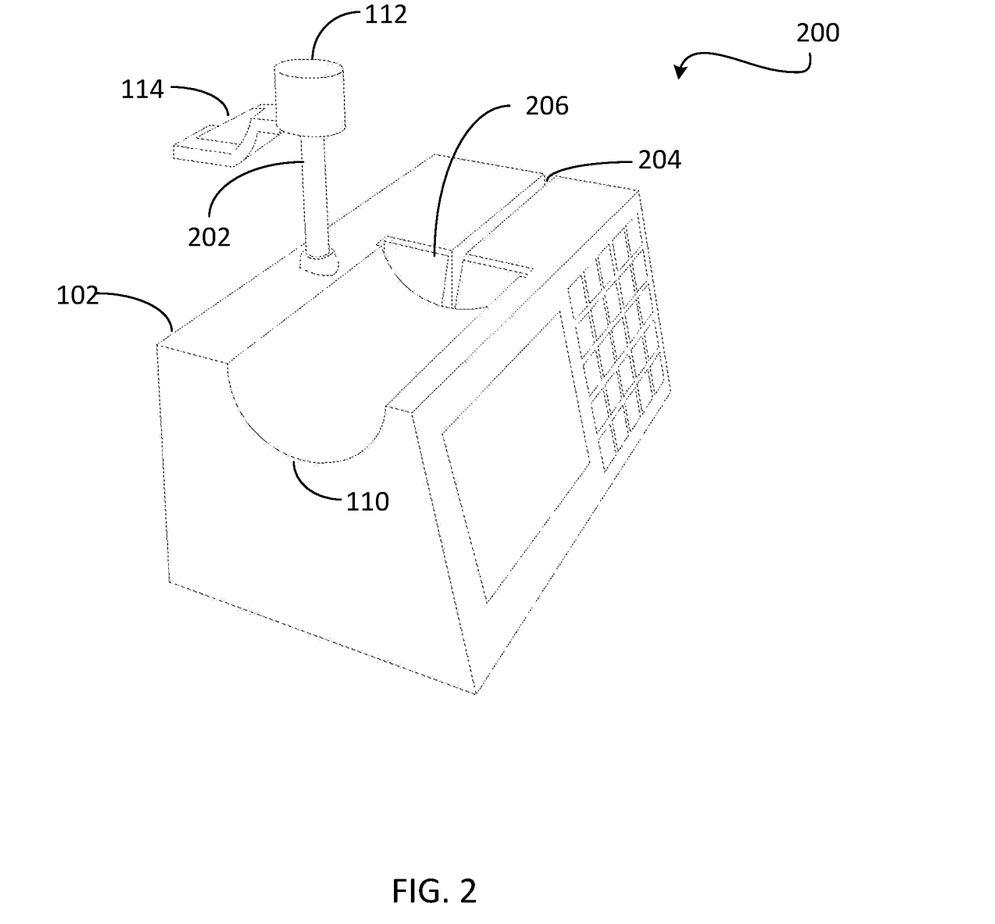
FIG. 2 is an illustration 200 of a syringe pump 102.

FIG. 2 is an illustration 200 of a syringe pump 102. The syringe pump 102 has a syringe barrel holder 206 at one end of the semi-circular seat 110 and a plunger slot 204 extending from the flange 206 to the opposite end of the semi-circular seat 110. When the syringe 104 is placed on the semi-circular seat 110, the flange 306 of the syringe 104 is placed in the flange holder 206 and one support of the plunger 116 is fitted into the plunger slot 204. The plunger slot 204 is in communication with the flange holder 206 and the semi-circular seat 110. The syringe holder 112 on the syringe pump 102 has a vertical pole 202 that extends from the syringe pump 102. The vertical pole 202 is controlled internally by a spring or spring-like mechanism that enables the holding arm 114 to apply a downward pressure on the syringe 104. The vertical pole 202 is also connected to a size sensor that indicates the diameter of the syringe 104 placed on the pump 102. Knowing the diameter of the syringe 104, the pump 102 can determine the speed for the movement of the plunger 116 based on the drug delivery parameter set through the input panel 106 by the medical staff.

Figure 3:
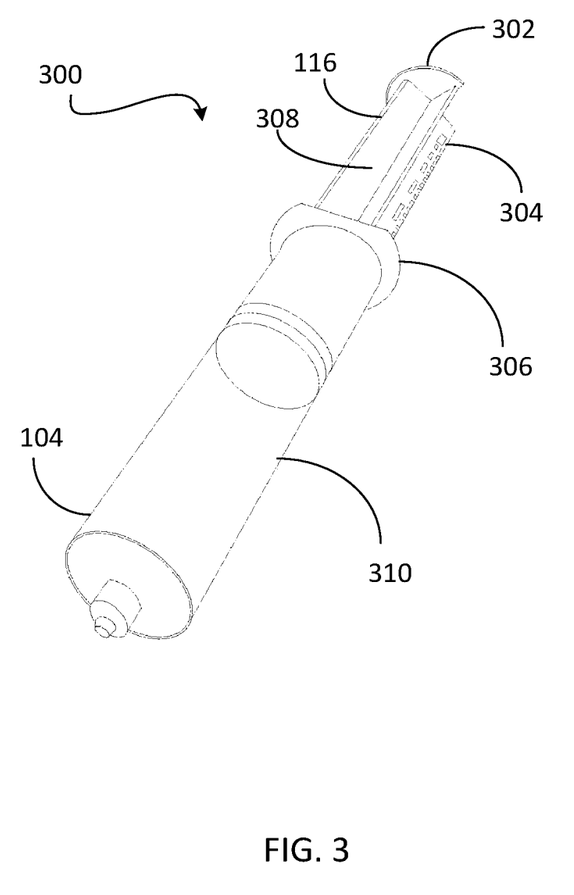
FIG. 3 is an illustration 300 of the syringe 104.

FIG. 3 is an illustration 300 of the syringe 104. The syringe 104 has a barrel 310 and a plunger 116. The barrel 310 has an end for delivering medication and another end with a flange 306. The plunger 116 has multiple plunger supports 308 and one of the plunger supports is a specially designed track 304 with a plurality of threads. The plunger 116 also has a semi-circular push-end 302. The track 304 is inserted into the plunger slot 204 and the threads engage a driving mechanism inside the syringe pump 102. The driving mechanism is a mechanical power driving system composed of a motor (not shown), a leadscrew 402, and a track 304 and moves the plunger in and out of the syringe 104 through the rotation of the leadscrew 402.

Figure 4:
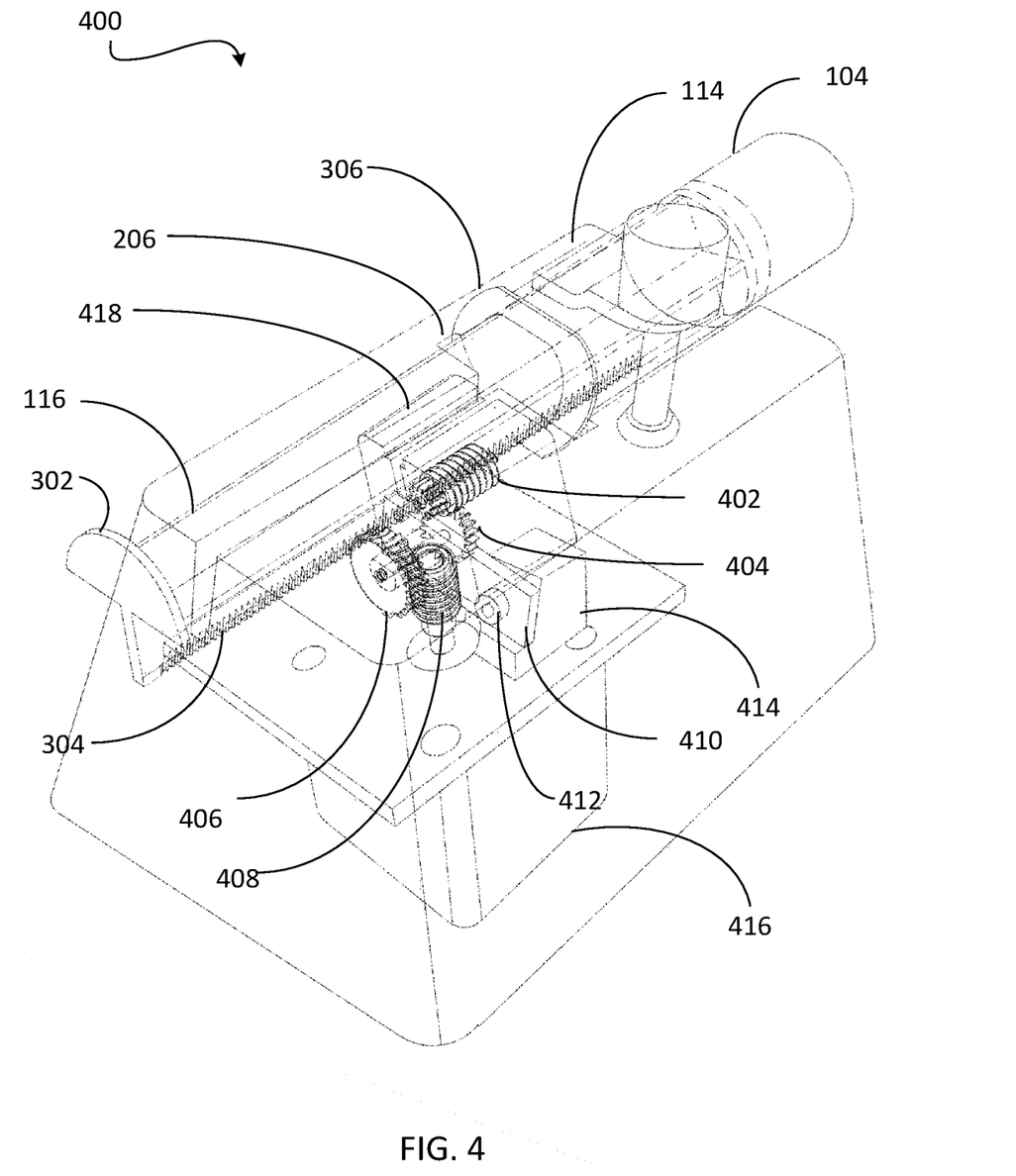
FIG. 4 is an illustration 400 of the driving mechanism in the pump 102.

FIG. 4 is an illustration 400 of the driving mechanism in the pump 102. When the syringe 104 is placed on the seat 110 of the pump 102 and secured by the holding arm 114, the track 304 on the plunger 116 is inserted into the plunger slot 204. There is a cage housing 418 inside the pump 102 and part of the track 304 on the plunger 116 fits in the cage housing 418. The driving mechanism inside the cage housing 418 has a leadscrew 402 for engaging the threads on the track 304. The leadscrew 402 is driven by an electrical motor 416 through a number of gears 406, 408 and a pinion 404. Because the syringe 104 is fixed on the pump 102 and the flange 306 is inserted into the flange holder 206, the rotation of the leadscrew 402 moves the plunger 116 in and out of the syringe 104. One end of the leadscrew 402 shaft pushes against a sensor plate 410 that is secured by a nut 412 to the mounting support 414. When the leadscrew 402 rotates and pushes the track 304, the resistance from the track 304 pushes the leadscrew 402 against the force sensing strain gage sensor plate 410 to produce an electrical signal, which is used to determine if there is any problem in the delivery of drug or if the plunger 116 hits the bottom of the syringe 104. When the thread 514 on the plunger is engaged with the leadscrew 402, the leadscrew thread will prevent the plunger from moving, which may be caused by external siphoning force. The pump 102 is equipped with a position sensor that determines the position of the plunger 116. The position sensor senses the positional patterns on the track 304 and determines the movement of the plunger 116. The position sensor also senses the proper loading and seating of the track 304 on the slot 204, which assures proper engagement between the track 304 and the leadscrew 402.

Figure 5:
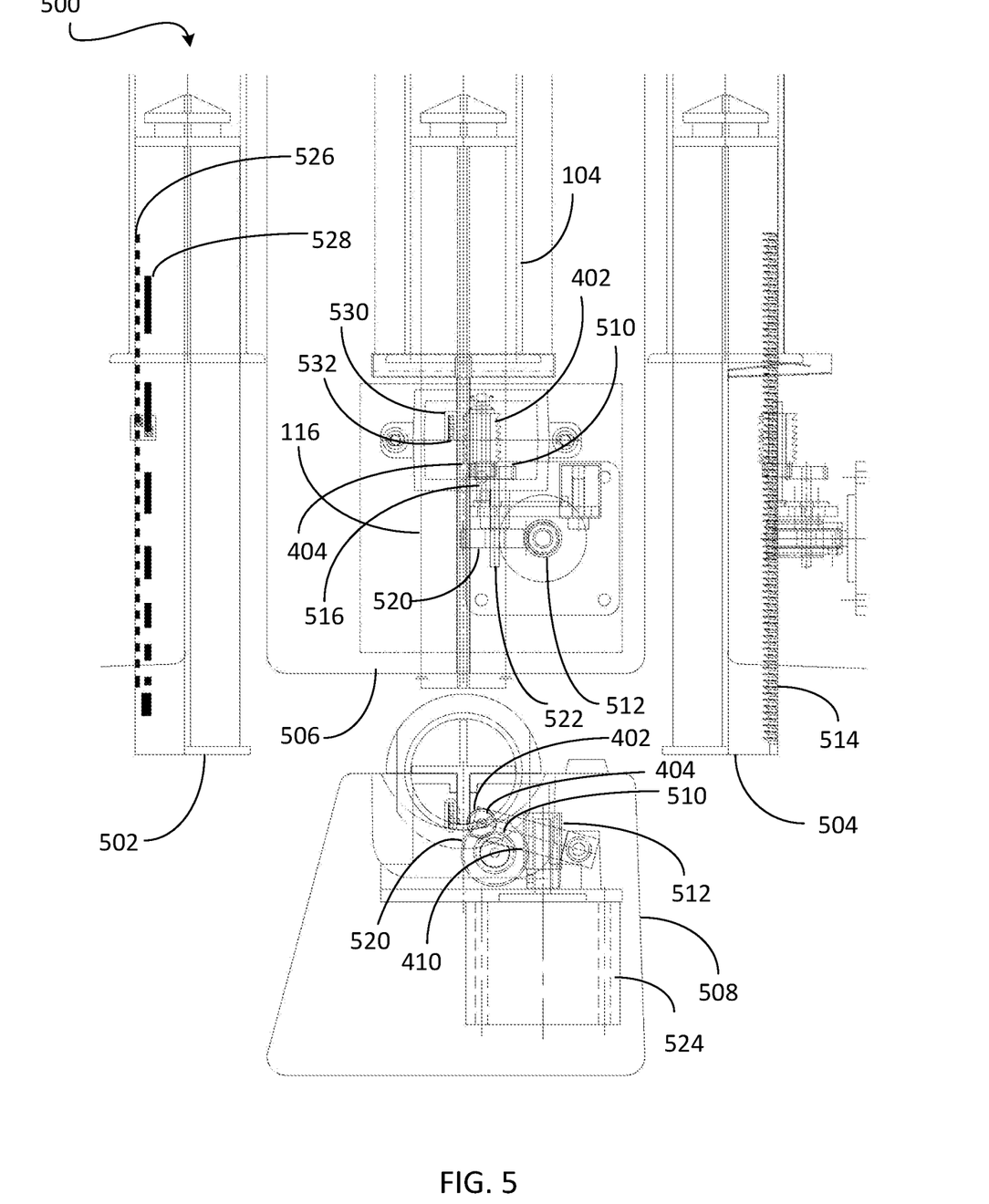
FIG. 5 shows an illustration 500 that includes a right side view 502 of the syringe 104, a left side view 504 of the syringe 104 mounted on the pump 102, a top view 506 of the syringe 104 mounted on the pump 102, and an elevation view of the syringe 104 mounted on the pump 102.

FIG. 5 shows an illustration 500 that includes a right side view 502 of the syringe 104, a left side view 504 of the syringe 104 mounted on the pump 102, a top view 506 of the syringe 104 mounted on the pump 102, and an elevation view of the syringe 104 mounted on the pump 102. The right side view 502 shows one of the plunger support 308 marked with two positional markings, 526, 528. The lower channel marking 526 is used to sense the proper advancement of the plunger track 304. If the plunger track 304 moves properly, the optical sensor 530 will generate a waveform as expected. The upper channel marking 528 is used to produce information about the current position of the plunger track 304. When the optical sensor 530 detects a transition from Dark to White or White to Dark, it signals a known position of the track 304. The exact current position can be determined at the next transition by measuring the motor steps needed between the two transitions. The optical sensor 530 senses 3 states: White, Black and None. The None state is that the sensor does not receive any reflection. This means that the plunger track 304 is not seated properly. Thus, the optical sensors can warn the user that the improper loading of the syringe plunger. The left side view 504 shows threads 514 on one of the plunger support 308.

The top view 506 shows a syringe 104 mounted on the pump 102 with the plunger 116 inserted into the plunger slot 204 and the cage housing 418 inside the pump 102. The leadscrew shaft 516, leadscrew 402, and pinion 404 are pressed fit together as an assembly. A motor 524 and the cage housing 418 are mounted onto a flat metal plate so that the worm gear 520 and the worm 512 are properly engaged. The whole assembly is mounted to the top housing with screws (Not shown) from the flat metal plate.

The force sensing mechanism is provided by the strain gage sensor plate 410 mounted on a mounting support 414 on the flat metal plate. The leadscrew shaft 516 is pressed onto the sensor plate 410. There is a bias spring (not shown) at the other end of the leadscrew shaft 516 to ensure that leadscrew shaft 516 is pressing positively on the sensor plate 410.

The cage housing 418 has a slot aligned with the plunger slot 204 for seating the plunge support 308. The cage housing 418 has an opening on one side of the plunger slot 204 for the leadscrew 402 to engage with threads of the plunger track 304. The cage housing 418 also has opening on the other side of the plunger slot 204 for optical sensors 530, 532 to sense the positional markings.

When in use, the syringe 104 with the special plunger 116 and loaded with the medication is placed on the pump 102. The syringe 104 is secured by the holding arm 114 and the flange 306 is fitted into the flange holder 206. The plunger 116 moves into the syringe 104 by rotation of the leadscrew 402 and forces the medication out of the syringe 104. The rotation of the leadscrew 402 is controlled by the gears and the electrical circuit (not shown) according to the input provided by the user through the input panel 106. The movement of the plunger 116 is controlled by the movement of the track 304. The rotation of the leadscrew 402 is also controlled by feedback of the strain gage sensor plate 410. When the plunger 116 reaches a point that it cannot move forward, the continuous rotation of the leadscrew 402 will force the leadscrew 402 against the strain gage sensor plate 410, generating a signal, which indicates the plunger 116 is no longer moving.

If the leadscrew 402 is rigidly engaged with a motor driving mechanism, it will not have free axial movement needed to produce a pressing force on the strain gage senor plate 410. To avoid the problem caused by the rigid engagement between the leadscrew 402, the gear 406 engages the pinion 404 mounted adjacent to the leadscrew 402 to allow the free axial movement of the leadscrew 402 to minimize the error in force sensing by the influence driving force on the leadscrew 402. If the worm gear 520 is directly mounted on the leadscrew shaft 516, the force from the leadscrew 402 cannot be accurately sensed by the sensor plate 410 when the worm gear 520 is turned by worm 512 due to the rigid angular teeth engagement between the worm gear 520 and worm 512 to impede the axial movement of the leadscrew shaft 516.

Figure 6A:
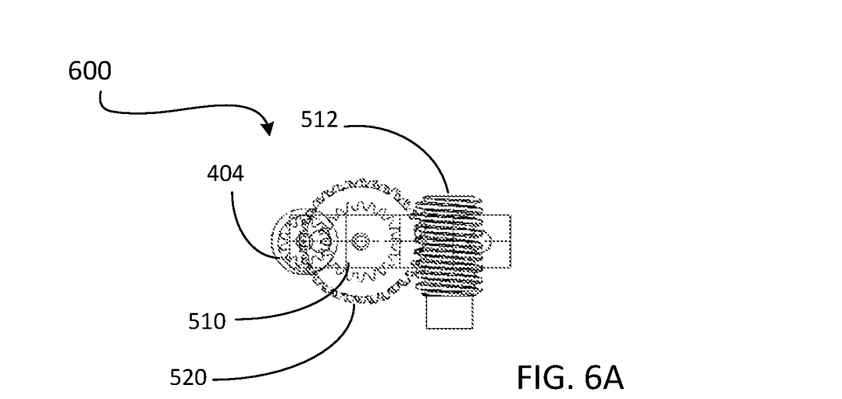
FIG. 6A shows an elevation view of the force sensing mechanism.
Figure 6B:
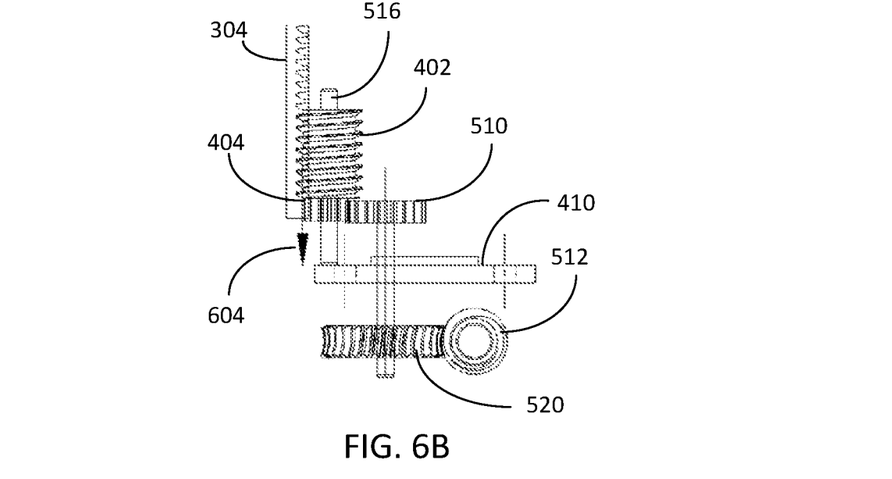
FIG. 6B shows a top view of the force sensing mechanism.

By adding a pinion 404 and a spur gear 510 between leadscrew 402 and worm gear 520, the axial movement is not significantly affected due to the parallel teeth engagement between the pinion 404 and the spur gear 510. It allows the transmission of rotation and not to impede the axial movement of the leadscrew shaft 516. The force sensing mechanism is better illustrated by FIGS. 6A and 6B. The teeth of the pinion 404 and the spur gear 510 engage each other and this enables transmission of the rotation without impeding the axial movement of the leadscrew shaft 402. The spur gear 510 and the worm gear 520 are mounted on the same axel, and this axel passes under the force sensing plate 410.

Because the plunger 116 is moved by the leadscrew 402 that is placed inside the pump 102 and close to the location where the flange 306 is secured, the size of the pump 102 can be made compact.

The driving method for the plunger 116 can be further described below. The rotation of the motor shaft turns the worm 512 and the worm gear 520. The dowel pin 522 couples the 520 worm gear with the spur gear 510 inside the cage 418. The spur gear 510 transfers the driving rotation from the worm gear 520 to the pinion 404 of the leadscrew 402 to create leadscrew rotation. The rotation of the leadscrew 402 drives the threads 514 of the plunger track 304 and creates liner movement of the plunger track 304.

The driving load at the plunger 116 pushes back the leadscrew 404 and transmits the load as a force pushing on the strain gage sensor plate 410 via the leadscrew shaft. To achieve this, the leadscrew 410 should have free axial movement from driving force from the motor.

The arrangement of the pinion 404 and the spur gear 510 has two purposes: (1) to produce desire the gear ratio, and (2) to allow free axial leadscrew movement to minimize the influence on force sensing due to the driving power. This is accomplished by the pinion and the spur gear pair, so that the driving rotating power from the worm gear is perpendicular to the leadscrew shaft. The friction influence on the axial movement of the leadscrew shaft is minimized.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Other modifications, variations, and alternatives are also possible. Accordingly, the claims are intended to cover all such equivalents. Dimensions in the drawings here presented are not to scale unless otherwise indicated. It is recognized that different features and steps depicted in different figures and described in different scenarios maybe combined or interchanged. Drug delivery is used to describe the general process of dispensing infusate to a patient and not limited to the delivery of medicine only.

What is claimed is:

1. A syringe pump for delivering medication through a syringe with a barrel with a flange and a plunger with a plurality of plunger supports and a semi-circular push end to deliver a drug to a patient comprising:
   a housing with a flange holder for receiving the flange of a syringe barrel and a plunger slot for receiving one of the plurality of plunger supports, the plunger slot extending along longitudinal direction of the syringe, the flange holder being a slot with semi circular form and the flange being inserted into the flange holder;
   an electrical motor disposed inside the housing;
   a plurality of gears driven by the electrical motor;
   a leadscrew with a leadscrew shaft connected to the plurality of gears;
   a cage housing for housing the leadscrew and for at least partially holding the plunger;
   a force sensing plate mounted on a mounting support inside the housing, and
   a spur gear and a worm gear mounted on an axel, and said axel passes under the force sensing plate;
   wherein
   the leadscrew shaft pushes against the force sensing plate, and the semi-circular push end of the plunger slides over the plunger slot when the plunger moves into the barrel of the syringe.

2. The syringe pump of claim 1, further comprising:
   a syringe holder with a vertical pole disposed on top of the housing; and
   a holding arm connected to the syringe holder,
   wherein the syringe holder moves vertically and the holding arm rotates around the vertical pole.

3. The syringe pump of claim 1, further comprising at least one optical sensor mounted inside the housing, facing the plunger.

4. The syringe pump of claim 3, wherein the at least one optical sensor senses markings on the plunger and determines a position of the plunger.

5. The syringe pump of claim 1, further comprising:
   a pinion mounted on the leadscrew shaft; and
   the spur gear being mounted in parallel to the pinion,
   wherein the spur gear drives the pinion and the pinion rotates the leadscrew.

6. The syringe pump of claim 1, wherein the housing further comprises a semi-circular seat for receiving the barrel of the syringe.

7. The syringe pump of claim 1, wherein the plunger slot is in communication with the flange holder.

8. The syringe pump of claim 1, wherein the plunger slot has a flat top surface that allows the semi-circular push-end of the syringe to advance toward the flange holder.

9. The syringe pump of claim 8, wherein the leadscrew shaft, leadscrew, and a pinion are pressed fit together as an assembly.

10. The syringe pump of claim 8, wherein the spur gear engages the pinion mounted adjacent to the leadscrew to allow free axial movement of the leadscrew.

11. The syringe pump of claim 10, wherein the free axial movement of the leadscrew minimizes the error in force sensing on the force sensing plate.

12. The syringe pump of claim 8, further comprises a syringe holder connected to the housing, the syringe having a holding arm and the holding arm being capable of moving up and down, when the holding arm is in a down position, the holding arm secures the syringe onto the housing.

13. The syringe pump of claim 8, wherein the holding arm rotates around the syringe holder.

14. The syringe pump of claim 8, further comprises a plunger slot disposed on the housing for receiving a plunger support.

15. A syringe pump for delivering medication through a syringe with a flange and a plunger with a plurality of plunger supports to deliver drug to a patient, one of the plunger supports having a track with a plurality of threads, comprising:

a housing with a flange holder for receiving the flange of the syringe barrel;
an electrical motor disposed inside the housing;
a plurality of gears driven by the electrical motor;
a leadscrew, with a leadscrew shaft, connected to the plurality of gears, the leadscrew engaging the threads on the track; and
a force sensing plate mounted on a mounting support and placed against the leadscrew,
wherein
when the leadscrew rotates and pushes the track through the threads, a resistance from the track pushes the leadscrew shaft against the force sensing plate.

* * * * *